US011129976B2

(12) United States Patent
Tanaka et al.

(10) Patent No.: US 11,129,976 B2
(45) Date of Patent: Sep. 28, 2021

(54) TEST METHOD

(71) Applicants: OSAKA UNIVERSITY, Suita (JP); NIPPON ZOKI PHARMACEUTICAL CO., LTD., Osaka (JP)

(72) Inventors: Hiroyuki Tanaka, Suita (JP); Tsuyoshi Murase, Suita (JP); Hideki Yoshikawa, Suita (JP); Mitsuru Naiki, Kato (JP); Tomonori Matsumoto, Kato (JP)

(73) Assignees: OSAKA UNIVERSITY, Suita (JP); NIPPON ZOKI PHARMACEUTICAL CO., LTD., Osaka (JP)

(*) Notice: Subject to any disclaimer, the term of this patent is extended or adjusted under 35 U.S.C. 154(b) by 435 days.

(21) Appl. No.: 16/079,721

(22) PCT Filed: Feb. 24, 2017

(86) PCT No.: PCT/JP2017/007203
§ 371 (c)(1),
(2) Date: Aug. 24, 2018

(87) PCT Pub. No.: WO2017/146230
PCT Pub. Date: Aug. 31, 2017

(65) Prior Publication Data
US 2019/0175894 A1    Jun. 13, 2019

(30) Foreign Application Priority Data
Feb. 24, 2016 (JP) .............. JP2016-032784

(51) Int. Cl.
| A61M 37/00 | (2006.01) |
| A61D 7/00 | (2006.01) |
| C12N 7/00 | (2006.01) |
| A61K 35/36 | (2015.01) |
| A01K 67/027 | (2006.01) |

(52) U.S. Cl.
CPC ..... *A61M 37/0069* (2013.01); *A01K 67/0273* (2013.01); *A61D 7/00* (2013.01); *A61K 35/36* (2013.01); *C12N 7/00* (2013.01); *A01K 2227/107* (2013.01); *A01K 2267/01* (2013.01); *A01K 2267/0387* (2013.01); *A61M 2037/0007* (2013.01); *C12N 2710/24111* (2013.01); *C12N 2710/24132* (2013.01)

(58) Field of Classification Search
CPC .......... A01K 2227/107; A01K 2267/01; A01K 2267/0387; A01K 67/0273; A61D 7/00; A61K 35/36; A61M 2037/0007; A61M 37/0069; A61P 11/02; A61P 17/00; A61P 17/04; A61P 19/02; A61P 25/02; A61P 25/04; A61P 29/00; A61P 37/08; C12N 2710/24111; C12N 2710/24132; C12N 7/00
See application file for complete search history.

(56) References Cited

U.S. PATENT DOCUMENTS

| 2002/0131953 A1* | 9/2002 | Takashima ..... A61K 39/001186 424/85.1 |
| 2006/0051375 A1 | 3/2006 | Cheung |
| 2016/0038548 A1* | 2/2016 | Kirn ................. A61K 49/0008 424/93.2 |

FOREIGN PATENT DOCUMENTS

| EP | 0348353 A2 | 12/1989 |
| EP | 1566178 A1 | 8/2005 |
| EP | 2174661 A1 | 4/2010 |
| EP | 3427726 A1 | 1/2019 |
| JP | S53-101515 A | 9/1978 |
| JP | S55-87724 A | 7/1980 |
| JP | H02-28119 A | 1/1990 |
| JP | H07-97336 A | 4/1995 |

OTHER PUBLICATIONS

Chen Z, et al The Extract of Inflamed Rabbit Skin Induced by Inoculation of Vaccinia Virus Possesses Antioxidant and Neuroprotective Effects in Acute Ischemic Stroke: J. Stroke and Cerebrovascular Diseases, 2009, 18(6) (Nov.-Dec.),pp. 475-481; doi: 10.1016/j.jstrokecerebrovasdis.2009.06.006. (Year: 2009).*
May 23, 2017 International Search Report issued in International Patent Application No. PCT/JP2017/007203.
May 23, 2017 Written Opinion issued in International Patent Application No. PCT/JP2017/007203.
Masaaki Takahara. "Basic Study on the Profitable Administration Method of Peplomycin, Especially Through Continuous Administration". Journal of the Japanese Stomatological Society, Oct. 1990, vol. 39, No. 4, pp. 907-931.
Yoko Suzuki et al. "Carbachol Induced Vagal Hyperactivity Stimulates Visceral Cell Proliferation in Mice". Japanese Journal of Applied Physiology, Jun. 1, 2008, vol. 38, No. 3, pp. 151-158.
Mami Mitani et al. "In Vivo Ni Okeru Sudachitin No Men'eki Chosetsu Sayo—Alzet Pump O Mochiita Kento-". The Japanese Journal of Nutrition and Dietetics, Sep. 24, 2015, vol. 73, No. 5 supplement, pp. 172.

(Continued)

*Primary Examiner* — Aaron J Kosar
(74) *Attorney, Agent, or Firm* — Oliff PLC

(57) ABSTRACT

The object of the present invention is to provide a test method using a novel administration method of an extract from inflamed tissues inoculated with vaccinia virus or a preparation containing the extract. It has been demonstrated that by sustainedly administering an extract from inflamed tissues inoculated with vaccinia virus or a preparation containing the extract by using a continuous administration device according to the present invention, a comparable effect is exerted at a very low dose compared with conventional administration methods such as oral administration. Therefore, the present invention can provide a test method using animals requiring less burden on a researcher, a treatment of patient at a low dose, and the like.

6 Claims, 8 Drawing Sheets

(56) References Cited

OTHER PUBLICATIONS

Jul. 17, 2019 Search Report issued in European Patent Application No. 17756664.3.

Bai Shan Wu et al. "Therapeutic Effect of Neurotropin by Continuous Epidural Injection in the Treatment of Postherpetic Neuralgia". Chinese Journal of Pain Medicine, Mar. 1, 2008, pp. 141-144, URL: <http://en.cnki.com.cn/Article_en/CJFDTOTAL-ZTYZ200803006.htm> [retrieved on Jun. 14, 2019].

Sep. 29, 2020 Office Action issued in European Patent Application No. 17756664.3.

Mitsuru Naiki et al. "Neurotropin Inhibits Experimental Allergic Encephalomyelitis (EAE) in Lewis Rats". Int. J. Immunopharmac., vol. 13, Nos. 2/3, 1991, pp. 235-243.

Takehiro Kawashiri et al. "Neurotropin Reverses Paclitaxel-Induced Neuropathy Without Affecting Anti-Tumour Efficacy". European Journal of Cancer, vol. 45, 2009, pp. 154-163.

Guangyi Zhao et al. "Intrathecal Lidocaine Neurotoxicity: Combination With Bupivacaine and Ropivacaine and Effect of Nerve Growth Factor". Life Sciences, vol. 112, 2014, pp. 10-21.

Yoshihisa Sugimura et al. "Protective Effect of Dexamethasone on Osmotic-Induced Demyelination in Rats". Experimental Neurology, vol. 192, 2005, pp. 178-183.

* cited by examiner

[Fig1]
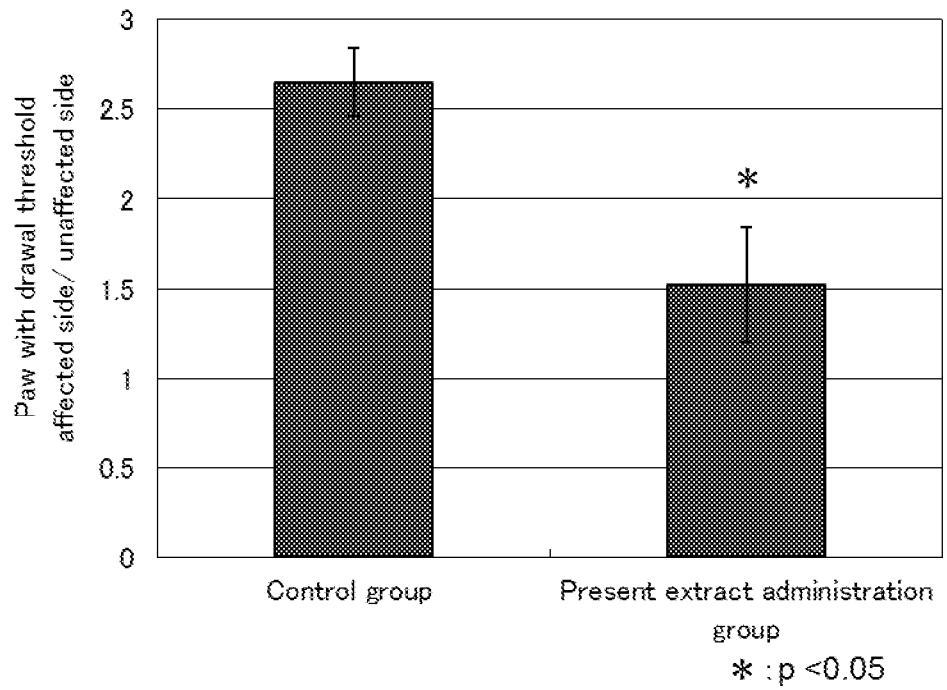
[Fig2]
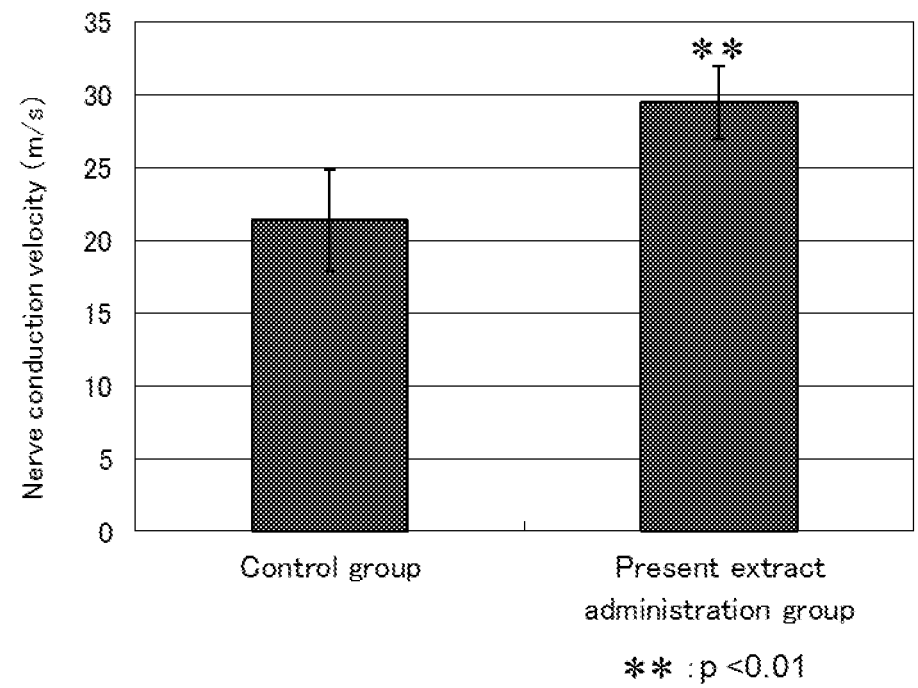

[Fig3]
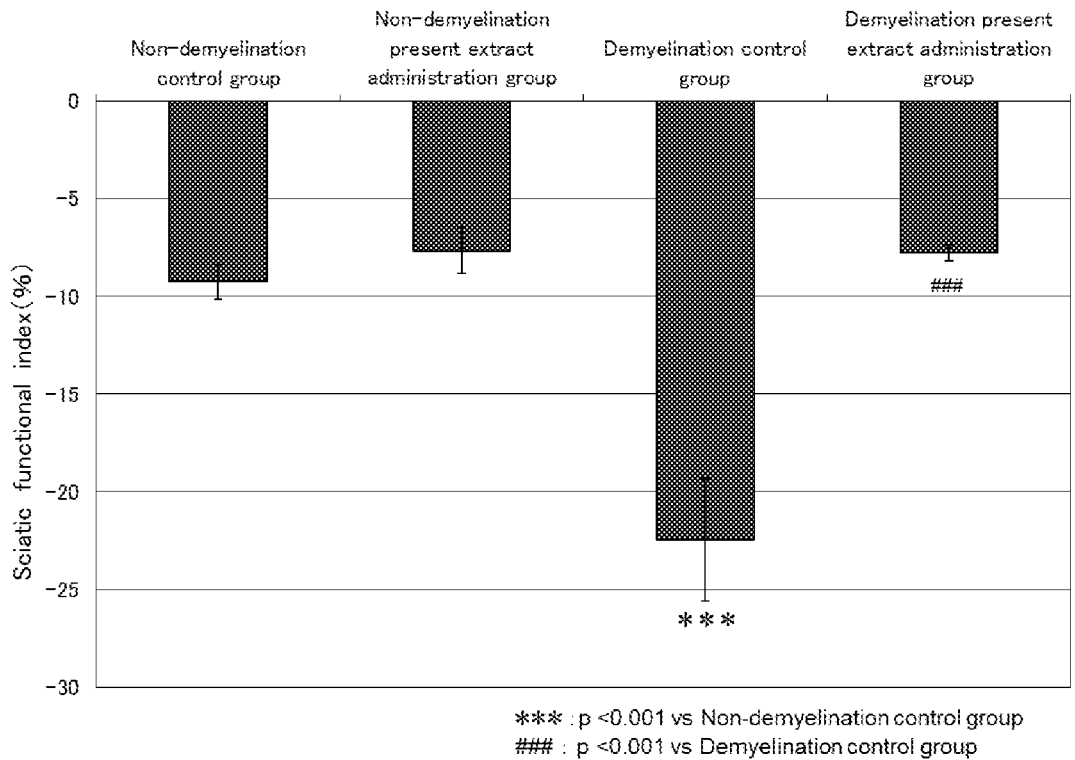
[Fig4]
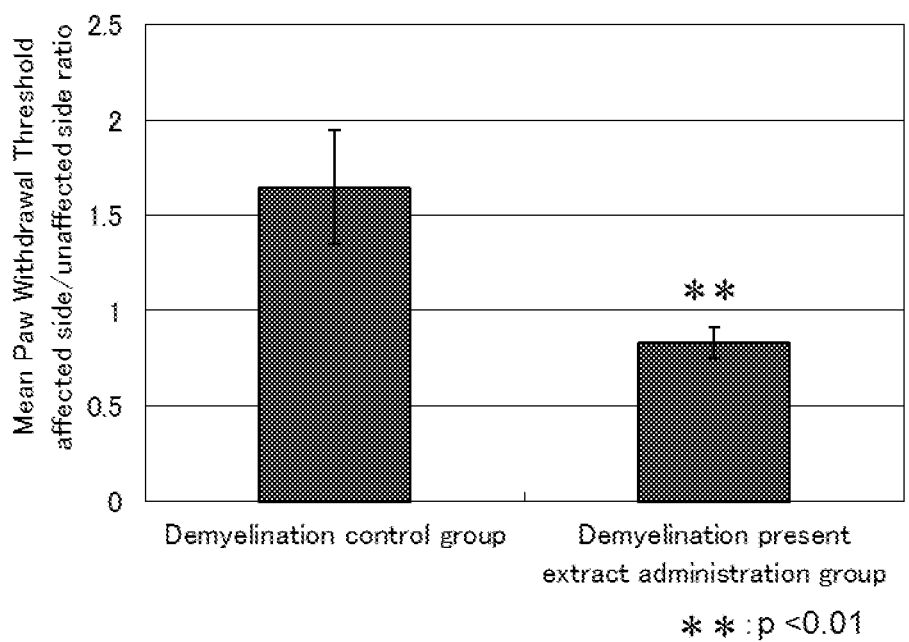

[Fig5]
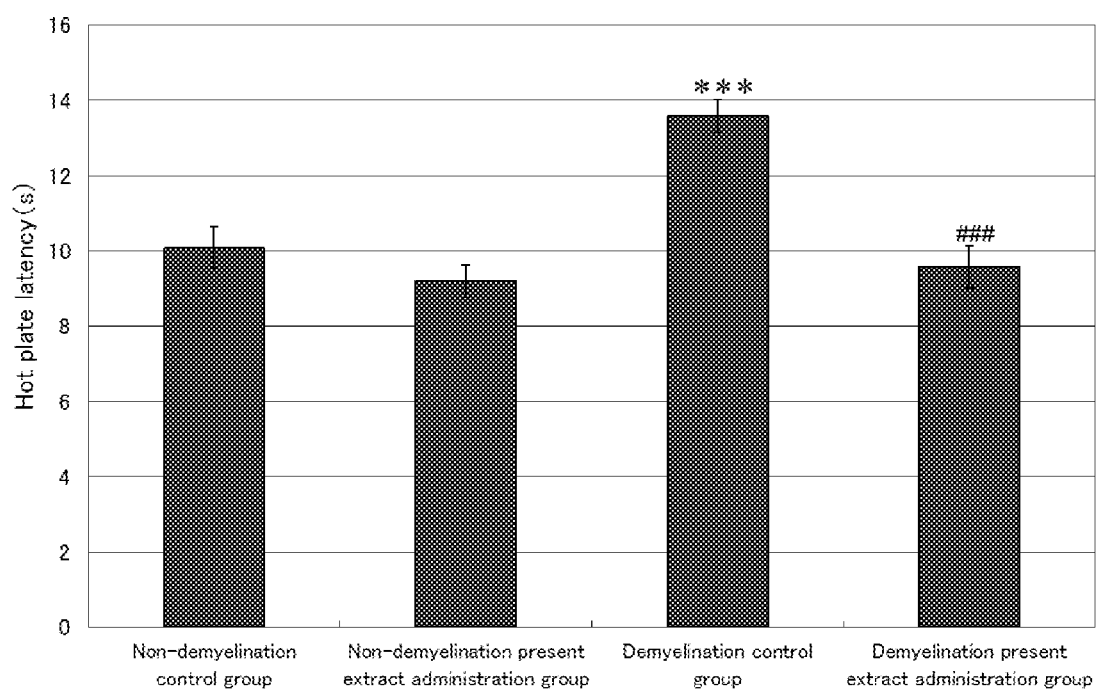

[Fig6]
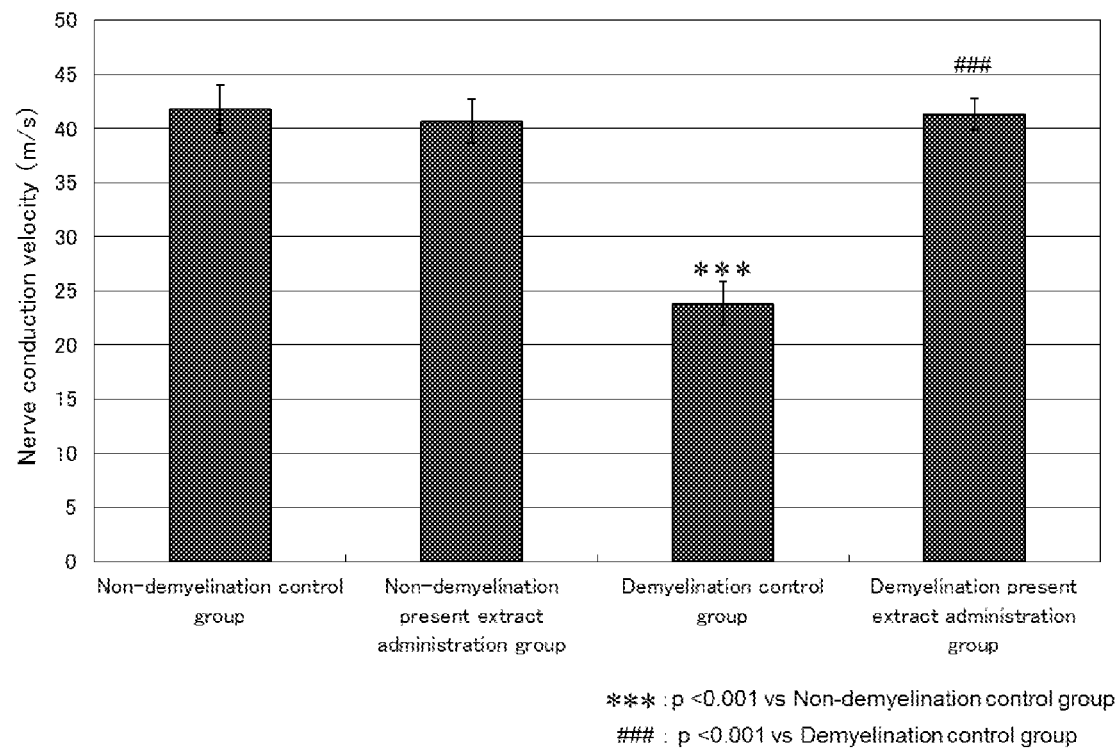

[Fig7]
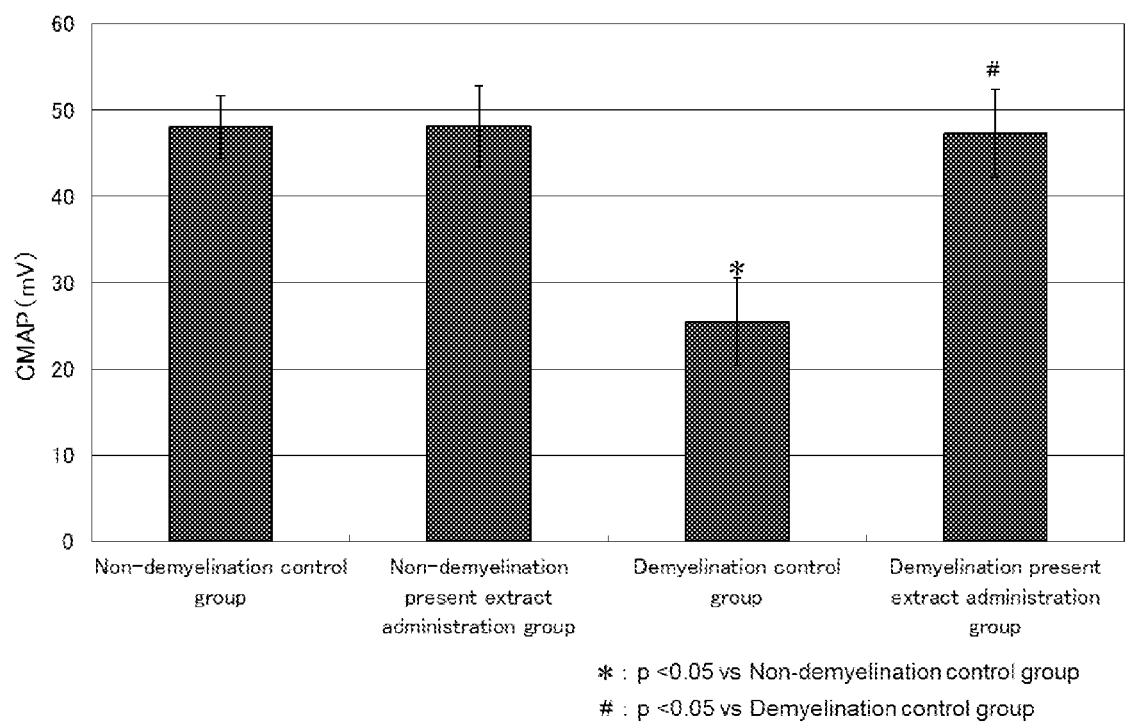

[Fig8]
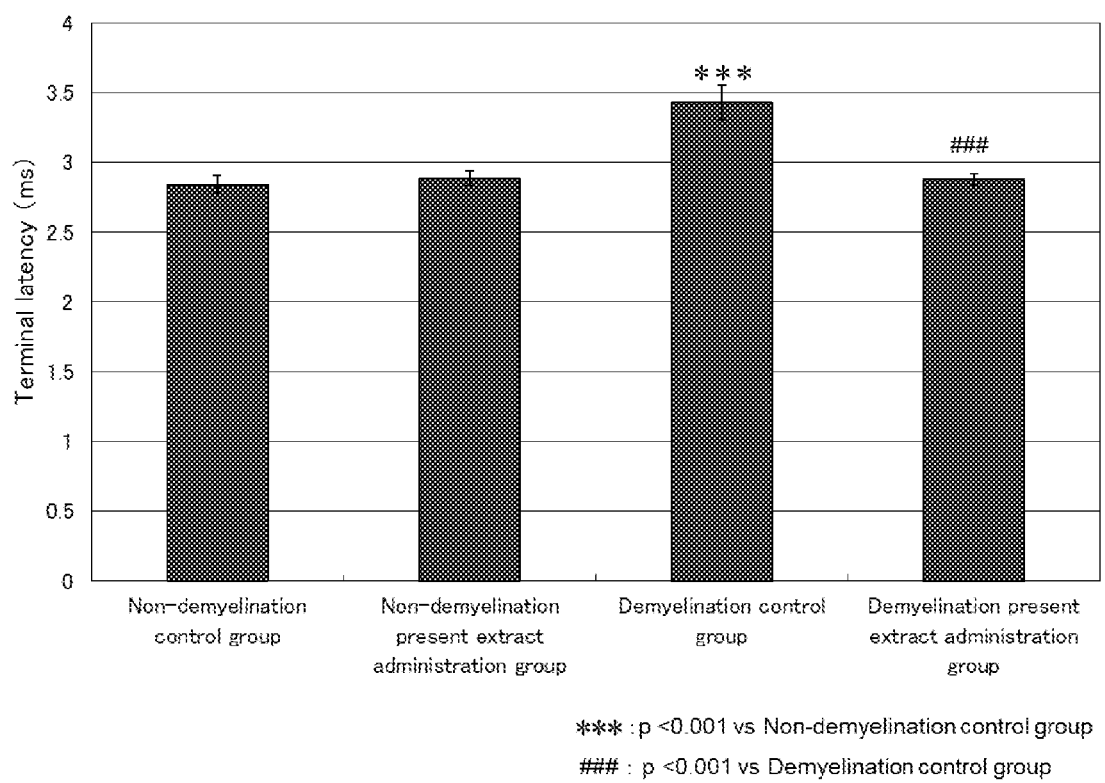

[Fig9]
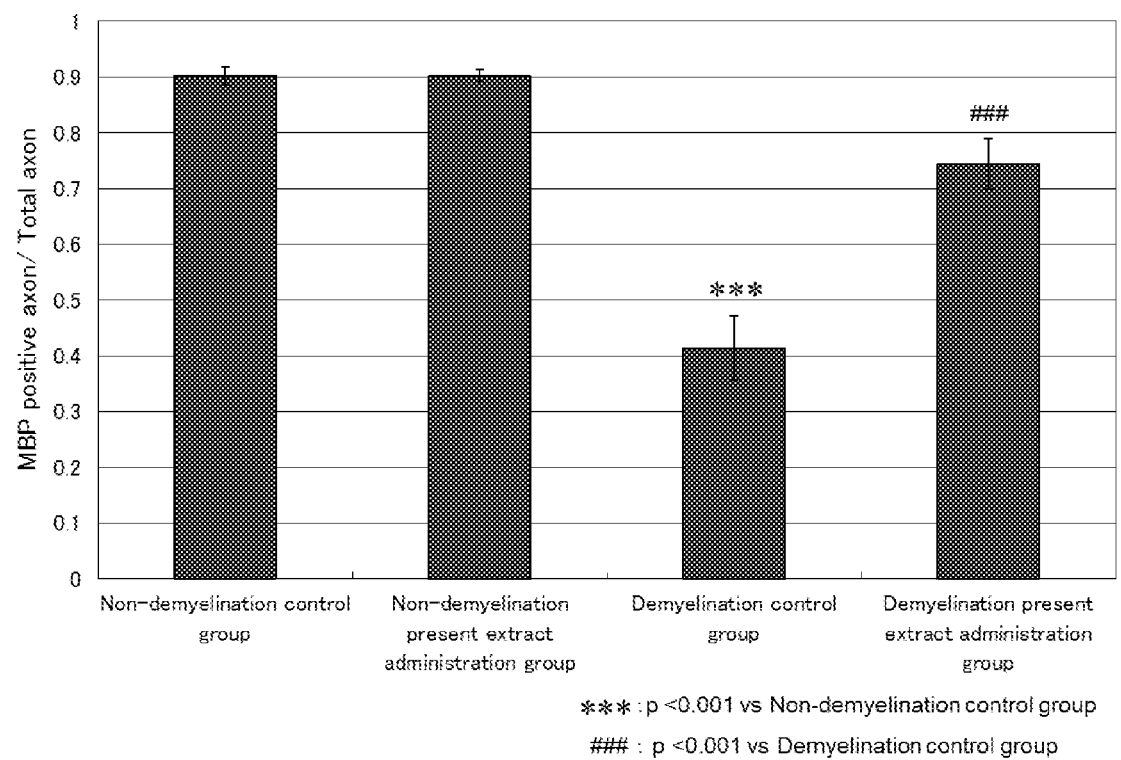

[Fig10]
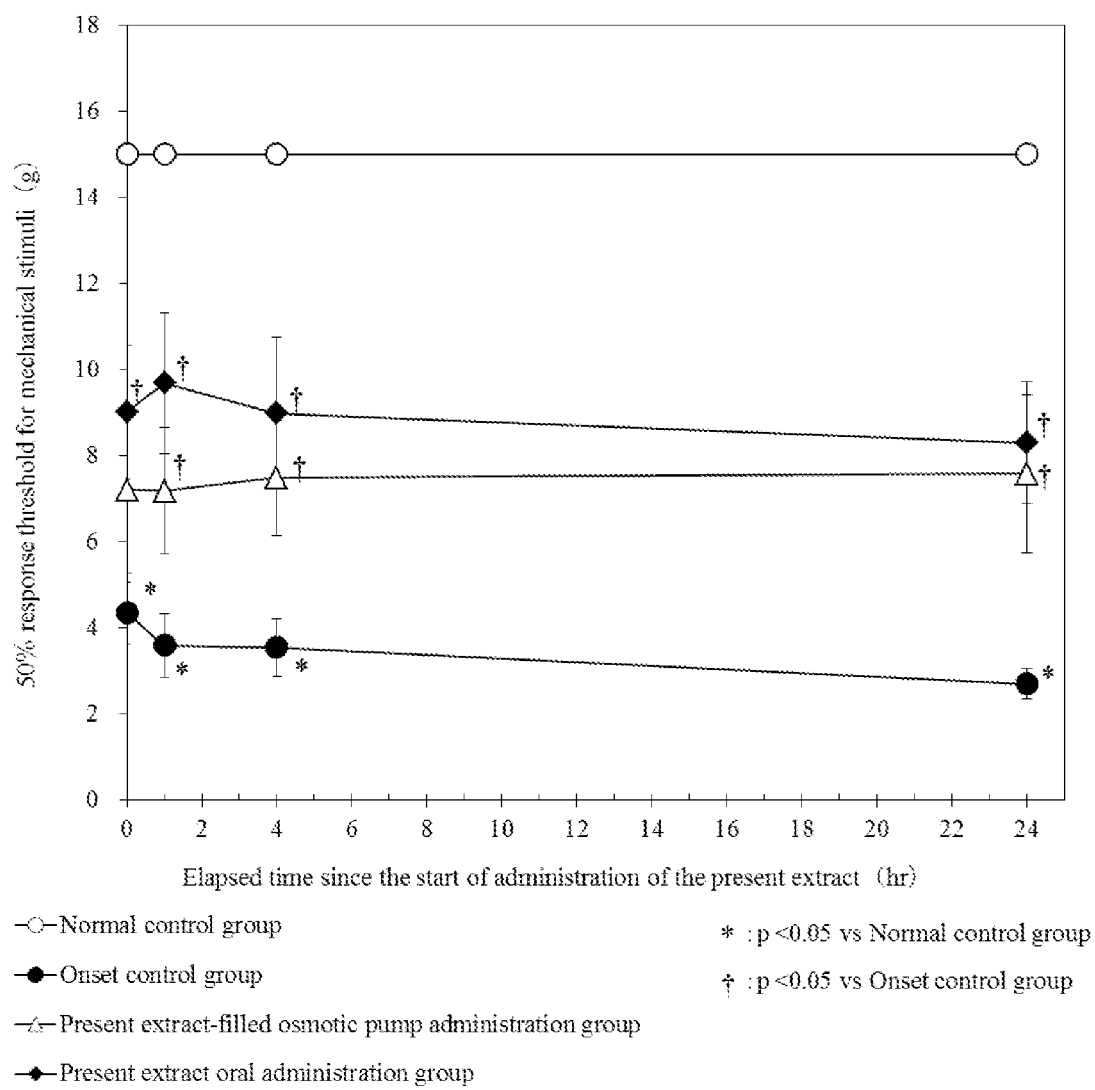

TEST METHOD

TECHNICAL FIELD

The present invention relates to a novel test method or the like using an extract from inflamed tissues inoculated with vaccinia virus (hereinafter, also referred to as "present extract") or a preparation containing the present extract (hereinafter also referred to as "present preparation", or the preparation together with the present extract can be referred to as "present extract or the like"). More specifically, the present invention relates to a test method featured by administering the present extract or the like using a device capable of continuous administration at an automatically controlled dose (hereinafter, referred to as "continuous administration device"), and a treatment method by the present extract or the like, and the like.

BACKGROUND ART

Conventionally, as an administration method in administering the present extract or the present preparation to a human or an animal other than a human, intravenous administration, intraperitoneal administration, intramuscular administration, subcutaneous administration, oral administration, and the like are known. When a human subject is administered with the present preparation, for example, the subject needs to receive an injection once a day to several days in the case of injections, or needs to take twice a day in the case of tablets. However, visiting a clinic every time to receive administration of injections is a great burden for a patient, and can cause the difficulty in continuing the treatment. Also, it can be difficult for a patient to obey the instruction not to forget taking a tablet a prescribed number of times every day. On the other hand, for investigation of the drug efficacy or the like of the present extract or the like by continuously administration of the present extract or the like to an animal other than a human, it is necessary to administer the present extract at a frequency of once a day. However, the task of administering the present extract or the like to an animal every day is complicated, and cannot be missed even in holidays, so that the task imposes burdens on researchers. Further, everyday administration of the present extract or the like brings great stress on laboratory animals, so that such administration is not desired also from the viewpoint of animal welfare.

As a method for continuously administering a human with a drug, for example, a method of intravenous drip infusion from a bag filled with the drug is known. Although an infusion device is also a measure capable of administering a drug continuously at a certain flow rate for a certain time, the motion of the subject is restricted, and the administration time is limited. Given these circumstances, the device called "infuser" has been also developed, and use of the infuser allows continuous administration of a drug for a period of about 1 week while the infuser is being carried. This device is a kind of the continuous administration devices. In order to continuously administer an animal other than a human with a drug for a long time, it is convenient to administer by means of a continuous administration device that automatically controls the dose. The continuous administration device may be a device that is attached to outside the animal body, or may be a device that is embedded inside the animal body. As a device that is attached to outside the animal body, for example, a product marketed as "Infusion pump MRBP-M/R" or "Infu-Disk (trademark)" is known. This product is accurate despite the simple structure, and is advantageous in that it can be easily attached or detached. On the other hand, using a continuous administration device that is embedded inside the body (normally subcutaneous) is advantageous in that the animal receiving administration can move more freely compared with the case of using the type attached to outside the body. One example of the continuous administration device that is embedded inside the body is a continuous administration device that operates by the osmotic pressure (hereinafter, referred to as "osmotic pump"), and such a continuous administration device is marketed, for example, as "alzet (registered trademark) osmotic pump". The osmotic pump operates by a difference in osmotic pressure between the osmotic layer inside the pump and the tissue environment in which the pump is embedded. That is, water flows into the pump through a semipermeable membrane that forms the surface of the pump, the flown-in water compresses a flexible reservoir filled with a drug, and thus the drug in the reservoir is pushed out at a certain flow rate. Other examples of the continuous administration device that is embedded inside the body include a product marketed as "iPRECIO (registered trademark) SMP/IMS-200". In this product, a micromotor is driven by a built-in battery, the drug is continuously discharged outside at a certain speed, and the drug can be supplemented even after the device is embedded inside the body. Therefore, this product is convenient when the administration spans a long period of time, or when a drug having different concentration or a different drug is administered from the middle. In the present invention, any of these types of continuous administration device can be used.

Many documents have disclosed conducting tests for various actions by administering the present extract or the present preparation according to the present invention to an animal or a human. For example, Patent Document 1 discloses that an analgesic action is exerted by single subcutaneous administration of the present extract. Patent Document 2 discloses that by intraperitoneally administering the present extract to a mouse once daily five times a week, an anticancer action, and a hepatic cirrhosis inhibitory action are exerted. Patent Document 3 discloses that a blood flow improving action is exerted by single oral administration of the present extract to a rat. Patent Document 4 discloses that by intravenously administering the present extract to a rat once a day, a peripheral circulatory disturbance ameliorating action is exerted. However, the test method, the treatment method, or the like of administering the present extract or the like by using a continuous administration device has not been disclosed, and thus the effect thereof has not been known.

PRIOR DOCUMENTS

Patent Documents

[Patent Document 1] Japanese Patent Laid-Open No. Sho-53-101515

[Patent Document 2] Japanese Patent Laid-Open No. Sho-55-87724

[Patent Document 3] Japanese Patent Laid-Open No. Hei-2-28119

[Patent Document 4] Japanese Patent Laid-Open No. Hei-7-97336

SUMMARY OF THE INVENTION

Problem to be Solved by the Invention

The present invention provides a test method of continuously administering a present extract or the like, and a treatment method by the present extract or the like, and the like.

Means for Solving the Problems

The present inventors have found that by sustainedly administering the present extract or the like by using a continuous administration device, a comparable or higher effect is obtained at a lower dose compared with the conventionally known administration method of the present extract or the like such as injection or oral administration, and a novel treatment method and the like by the present extract or the like based on this, and have accomplished the present invention.

Advantages of the Invention

The present invention has revealed that it is useful to conduct tests, experiments, researches, and the like (in the present application, simply referred to as "test") by the method of sustainedly administering the present extract or the like to an animal by using a continuous administration device. As a result, it is possible to confirm the known actions of the present extract or the like at a lower dose compared with the conventional administration methods. Also, there is a possibility that a novel action that has not been recognized by the conventional administration methods will be discovered. Further, while an operation of administering the present extract or the like every day or at a certain frequency has been required conventionally, the present invention can dramatically reduce the amount of work of the researcher because the administration operation becomes unnecessary for several days to several months. Further, since the load and stress on animals are reduced, the method is useful from the viewpoint of the animal ethics. Further, in humans, it is expected that administration of the present preparation by the continuous administration device contributes to improvement in continuous therapeutic effect in the patient. Since the present preparation is a drug that has longtime usage records and has high safety, the treatment by the present invention has very high practicality.

In the present invention, "continuous administration" refers to sustainedly administering a drug into a body at a certain speed (flow rate) for a certain time or longer, and "continuous administration device" refers to a device enabling continuous administration automatically, and can be of any type. For example, regarding an externally-attached type "Infu-Disk (trademark)", a product with a flow rate of 0.03 to 1.0 mL/hour (liquid amount 5 mL, use time 5 to 167 hours) and a product with a flow rate of 0.03 to 4.0 mL/hour (liquid amount 10 mL, use time 2.5 to 333 hours) are sold. On the other hand, regarding a body-embedded type "alzet (registered trademark) osmotic pump", twelve products of a flow rate ranging from 0.11 to 10.0 µL/hours and a use time ranging from 1 day to 6 weeks are sold. "iPRECIO (registered trademark) SMP/IMS-200" is designed to be usable for a use time ranging from 1 week to 6 months at a flow rate of 1.0 to 30.0 µL/hour (liquid amount 0.9 mL, about 5 mL at maximum by supplement). All of these devices can be used as a continuous administration device in the present invention.

BRIEF DESCRIPTION OF DRAWINGS

FIG. 1 shows a result of examination for the effect of continuous administration of the present extract on the paresthesia (torpor) occurring by sciatic nerve crush injury.

FIG. 2 shows a result of examination for the effect of continuous administration of the present extract on the dysfunction of a sensory nerve occurring by sciatic nerve crush injury.

FIG. 3 shows a result of examination for the effect of continuous administration of the present extract on the motor dysfunction occurring by administration of lysophosphatidyl choline (LPC).

FIG. 4 shows a result of examination for the effect of continuous administration of the present extract on the paresthesia (torpor) occurring by administration of LPC.

FIG. 5 shows a result of examination for the effect of continuous administration of the present extract on the thermal paresthesia (torpor) occurring by administration of LPC.

FIG. 6 shows a result of the effect of continuous administration of the present extract on the dysfunction of a sensory nerve occurring by administration of LPC, examined by using nerve conduction velocity (NCV) as an index.

FIG. 7 shows a result of the effect of continuous administration of the present extract on the dysfunction of a sensory nerve occurring by administration of LPC, examined by using compound muscle action potentials (CMAP) as an index.

FIG. 8 shows a result of the effect of continuous administration of the present extract on the dysfunction of a sensory nerve occurring by administration of LPC, examined by using terminal latency (TL) as an index.

FIG. 9 shows a result of examination for the effect of continuous administration of the present extract on the remyelination of a nerve axon after nerve demyelination by administration of LPC.

FIG. 10 shows a result of examination for the effect of continuous administration of the present extract on the paresthesia (hypersensitivity) occurring by administration of paclitaxel.

MODE FOR CARRY OUT THE INVENTION

The present extract is an extract containing a non-protein active substance extracted and separated from inflamed tissues of an animal having developed pox by being inoculated with vaccinia virus. The present extract is in liquid when it is extracted; however, the present extract may be made solid by drying. The present preparation is very useful as pharmaceuticals. One specific product that is manufactured and sold in Japan by the applicant as the present preparation is "Preparation containing an extract from inflamed rabbit skin inoculated with vaccinia virus" (trade name: NEUROTROPIN [registered trademark]) (hereinafter, referred to as "NEUROTROPIN"). NEUROTROPIN includes injections and tablets, both of which are ethical drugs.

Indications of NEUROTROPIN injection are "low back pain, cervicobrachial syndrome, symptomatic neuralgia, itchiness accompanied by skin diseases (eczema, dermatitis, urticaria), allergic rhinitis and sequelae of subacute myelo-optico-neuropathy (SMON) such as coldness, paresthesia and pain". Indications of NEUROTROPIN tablet are "postherpetic neuralgia, low back pain, cervicobrachial syndrome, periarthritis scapulohumeralis and osteoarthritis". Present preparation has been created by the applicant and developed as a drug, and has been appreciated for its excellent advantage for efficacy and safety, sold for many years and established a firm position in the Japanese pharmaceutical market.

The extract from inflamed tissues inoculated with vaccinia virus used in the present invention can be obtained by the following manner: inflamed tissues inflamed by the inoculation with vaccinia virus is crushed; an extraction solvent is added to remove the tissue fragments; then deproteinization is carried out; the deproteinized solution is adsorbed onto an adsorbent; and then the active ingredient is eluted. for example, according to the following process.

(A) Inflamed skin tissues of rabbits, mice or the like by the inoculation with vaccinia virus are collected, and the inflamed tissues are crushed. To the crushed tissue an extraction solvent such as water, phenolated water, physiological saline or phenol-added glycerin water is added. Then, the mixture is filtered or centrifuged to obtain an extraction liquid (filtrate or supernatant).

(B) The pH of the extraction liquid is adjusted to be acidic and the liquid is heated for deproteinization. Then, the deproteinized solution is adjusted to be alkaline, heated, and then filtered or centrifuged.

(C) The obtained filtrate or supernatant is made acidic and adsorbed onto an adsorbent such as activated carbon or kaolin.

(D) To the adsorbent, an extraction solvent such as water is added, the pH is adjusted to alkaline, and the adsorbed component is eluted to obtain the extract from inflamed tissues inoculated with vaccinia virus. Subsequently, as desired, the eluate may be evaporated to dryness under reduced pressure or freeze-dried to give a dried material.

As for animals in order to obtain the inflamed tissues by the inoculation of vaccinia virus, various animals that is infected with vaccinia virus such as rabbits, cows, horses, sheep, goats, monkeys, rats or mice can be used, and preferred inflamed tissues are inflamed skin tissues of rabbits. With regard to a rabbit, any rabbit may be used so far as it belongs to Lagomorpha. Examples thereof include Oryctolagus cuniculus, domestic rabbit (domesticated Oryctolagus cuniculus), hare (Japanese hare), mouse hare and snowshoe hare. Among them, it is appropriate to use domestic rabbit. In Japan, there is family rabbit called "Kato" which has been bred since old time and frequently used as livestock or experimental animal and it is another name of domestic rabbit. There are many breeds in domestic rabbit and the breeds being called Japanese white and New Zealand white are advantageously used.

Vaccinia virus used herein may be in any strain. Examples thereof include Lister strain, Dairen strain, Ikeda strain, EM-63 strain and New York City Board of Health strain.

As to basic extracting steps (A) to (D) of the above-described for the present extract can be carried out in more detail, the following steps are used for example.

About step (A):

The inflamed skin tissues of rabbits by the intradermal inoculation of vaccinia virus are collected. The collected skin tissues are washed and disinfected using a phenol solution, etc. This inflamed skin tissues are crushed and an extraction solvent in 1- to 5-fold thereof by volume is added thereto. Here, the term "crush" means to finely break down into minces using a mincing machine or the like. As to the extraction solvent, there may be used distilled water, physiological saline, weakly acidic to weakly basic buffer, etc. and bactericidal/antiseptic agent such as phenol, stabilizer such as glycerin, salts such as sodium chloride, potassium chloride or magnesium chloride, etc. may be appropriately added thereto. At that time, it is also possible that the cell tissue is destroyed by a treatment such as freezing/melting, ultrasonic wave, cell membrane dissolving enzyme or surfactant so as to make the extraction easier. The resulting suspension is allowed to stand for 5 to 12 days. During that period, the suspension may be heated at 30 to 45° C. with or without appropriate stirring. The resulting liquid is subjected to a treatment for separating into solid and liquid (filtered or centrifuged, etc.) to remove the tissue fragments whereupon a crude extract (filtrate or supernatant) is obtained.

About step (B)

The crude extract obtained in step (A) is subjected to a deproteinizing treatment. The deproteinization may be carried out by a known method which has been usually conducted and a method such as heating treatment, treatment with a protein denaturant (such as acid, base, urea, guanidine or an organic solvent including acetone), isoelectric precipitation or salting-out may be applied. After that, a common method for the removal of insoluble matters such as filtration using filter paper (such as cellulose or nitrocellulose), glass filter, Celite or Seitz filter, ultrafiltration or centrifugation is conducted to give a filtrate or a supernatant wherefrom the separated insoluble protein is removed.

About step (C)

The filtrate or supernatant obtained in step (B) is adjusted to acidic or, preferably, to pH 3.5 to 5.5 to conduct an operation of adsorbing with an adsorbent. Examples of the usable adsorbent include activated carbon and kaolin. An adsorbent is added to the extract followed by stirring or the extract is passed through a column filled with an adsorbent so that the active ingredient can be adsorbed with the adsorbent. When an adsorbent is added to the extract, the adsorbent with which the active ingredient is adsorbed can be obtained by means of filtration, centrifugation, etc. to remove the solution.

About step (D)

For elution (desorption) of the active ingredient from the adsorbent obtained in step (C), an elution solvent is added to said adsorbent and adjusted to basic or, preferably, to pH 9 to 12, elution is conducted at room temperature or with suitable heating, or with stirring, and then the adsorbent is removed by a common method such as filtration or centrifugation. As to the extraction solvent used therefore, there may be used a basic solvent such as water, methanol, ethanol, isopropanol or the like adjusted to basic pH or an appropriate mixed solvent thereof and preferably, water adjusted to pH 9 to 12 may be used. Amount of the extracting solvent may be appropriately set. In order to use the eluate obtained as such as a drug substance, the pH is appropriately adjusted to nearly neutral or the like whereby an extract from inflamed skins of rabbits inoculated with vaccinia virus (the present extract) can be finally obtained.

Since the present extract is liquid at the stage of being prepared, it is also possible that said extract is appropriately concentrated or diluted to make into a desired concentration. When a preparation is manufactured from the present extract, it is preferred to apply a sterilizing treatment with heating. For making into an injectable preparation, it is possible to add sodium chloride or the like so as to prepare a solution being isotonic to physiological saline. It is also possible that the present extract is administered in a liquid or gel state. Furthermore, the present extract may be subjected to an appropriate operation such as concentration to dryness to prepare a solid preparation for oral administration such as a tablet. Specific methods for the manufacture of solid preparation for oral administration from the present extract are disclosed in the specifications of Japanese Patent Nos. 3,818,657 and 4,883,798. The present preparation includes an injectable preparation, a solid preparation for oral administration, etc. prepared as such. In addition, the present preparation may be topically applied where to make Muse cells migrate by use of a catheter.

Hereinafter, examples of methods for producing the present extract as well as clinical evaluation concerning novel pharmacological activity of the extract, the promoting migration of pluripotent stem cells, are described. The present invention is not intended to be limited to the descriptions in Examples.

EXAMPLES

Example 1

Manufacture of the Present Extract

Skins of healthy adult rabbits were inoculated with vaccinia virus intradermally and the inflamed skins were cut and collected. The collected skins were washed and disinfected by a phenol solution, an excessive phenol solution was removed and the residue was crushed. A phenol solution was added thereto and mixed therewith and the mixture was allowed to stand for 3 to 7 days, and further heated at 35 to 40° C. together with stirring for 3 to 4 days. After that, an extracted solution obtained by a solid-liquid separation was adjusted to pH 4.5 to 5.2 with hydrochloric acid, heated at 90 to 100° C. for 30 minutes and filtered to remove protein. The filtrate was adjusted to pH 9.0 to 9.5 with sodium hydroxide, heated at 90 to 100° C. for 15 minutes and subjected to a solid-liquid separation.

The resulting deproteinized solution was adjusted to pH 4.0 to 4.3 with hydrochloric acid, activated carbon in an amount of 2% to the mass of the deproteinized solution was added thereto and the mixture was stirred for 2 hours and subjected to the solid-liquid separation. Water was added to the collected activated carbon followed by adjusting to pH 9.5 to 10 with sodium hydroxide and the mixture was stirred at 60° C. for 90 to 100 minutes and centrifuged to give a supernatant. Water was added again to the activated carbon precipitated upon the centrifugation followed by adjusting to pH 10.5 to 11 with sodium hydroxide and the mixture was stirred at 60° C. for 90 to 100 minutes and centrifuged to give a supernatant. Both supernatants were combined and neutralized with hydrochloric acid to give the present extract.

Example 2

Test Method and Test Result

Next, the test method and one example of the test result of the pharmacological test of administering the present extract obtained in Example 1 by means of a continuous administration device are shown.

A dose of the present extract per 1 kg of the body weight administered to rats by the osmotic pump was calculated from the body weight at the start of administration for Test examples 1 and 2, and from an average body weight during the administration period for Test example 3.

Test Example 1

Evaluation in Sciatic Nerve Crush Injury Model

Using a sciatic nerve crush injury model which is a peripheral nerve disorder model by physical actions, effects of the present extract on paresthesia (hypesthesia), motor dysfunction, and electrophysiological disorders which are symptoms by peripheral nerve disorder, and on regeneration from the nerve disorder were investigated. The present extract was continuously administered to rats by using an osmotic pump, and a von Frey test and an electrophysiological evaluation were conducted.

(1) Preparation of Sciatic Nerve Crush Model Rats and Administration of Present Extract An osmotic pump (product name: alzet [registered trademark], model: 2ML2, product of DURECT) was filled with saline, or the present extract, and stood still overnight in saline at 37° C. Male Wistar rats aged 6 weeks were deeply anesthetized using intraperitoneal administration of a mixed anesthetic of midazolam (2 mg/kg), butorphanol (2.5 mg/kg), and medetomidine (0.15 mg/kg). The left sciatic nerve of rats was exposed and a crush injury was applied with a pair of forceps at 5 mm distal from the sciatic notch. The crushing time was 10 seconds, the number of crushing operations was three, and the interval of the crushing operations was 10 seconds. The fascia and skin were sutured with a 4-0 nylon suture. Either a saline-filled osmotic pump or a present extract-filled osmotic pump (12 NU/kg/day) was placed subcutaneously in the back of rats. Experimental rats were divided into the following two groups.

(1) Control group: sciatic nerve crush injury is applied, and saline is systemically administered (2) Present extract administration group: sciatic nerve crush injury is applied, and the present extract is systemically administered The osmotic pump was indwelled for 2 weeks, and the osmotic pump was replaced, and further indwelled for 2 weeks, and thus the present extract or saline was continuously administered for 4 weeks.

(2) Von Frey Test

To evaluate the sensory function, at 4 weeks after the operation, hind paw withdrawal thresholds to mechanical stimuli (mechanical hind paw withdrawal thresholds) were measured by using von Frey filaments (0.008 g to 26 g, product name: TouchTest [registered trademark]), product of North Coast Medical). Rats were allowed to walk on the mesh fence, and a pressure was applied on the plantar surface with the von Frey filaments, and the value at which the rat had avoiding reaction was recorded. For evaluation, measurement was conducted on each of the unaffected side and the affected side, and the affected side/unaffected side ratio was calculated and evaluated.

Test Result

One example of the result of the above test is shown in FIG. 1.

The affected side/unaffected side ratio of hind paw withdrawal thresholds to mechanical stimuli (mechanical hind paw withdrawal thresholds) which is a functional evaluation of a sensory nerve significantly recovered and the paresthesia (hypesthesia) ameliorated in the present extract administration group compared with the control group.

(3) Electrophysiological Evaluation

Rats after a lapse of 4 weeks from the operation were sedated with an anesthetic, and placed in the prone position on the operating table. The left sciatic nerve and the left tibialis anterior muscle were exposed. Stimuli were applied on a proximal site and on a distal site to the sciatic nerve crush injury site with a bipolar electrode, and NCV was calculated from the respective measurements. For measurement and evaluation, a data recording and analyzing system PowerLab 2/26 (AD Instruments) was used.

Test Result

One example of the result of the above test is shown in FIG. 2. Significant recovery of NCV was observed and the electrophysiological function improved in the present extract administration group compared with the control group.

Test Example 2

Evaluation in Rat Sciatic Nerve Local Demyelination Model

Using an LPC-induced demyelination model which is a demyelination disease model, effects of the present extract on paresthesia (hypesthesia) which is a symptom by peripheral nerve disorder, paresthesia (hypesthesia) to a thermal stimulus, motor dysfunction, and electrophysiological disorders, and on nerve recovery from the nerve disorder were investigated. In the same manner as in the above Test example 1(1), the present extract was continuously administered to rats by using an osmotic pump, and evaluation of the sciatic function index, the von Frey test, the hot plate test, the electrophysiological evaluation, and the immunohistological evaluation were conducted.

(1) Preparation of Sciatic Nerve Local Demyelination Model Rats and Administration of Present Extract In the same manner as in Test example 1, an osmotic pump (product name: alzet [registered trademark], model: 2ML1, product of DURECT) was filled with saline or the present extract, and stood still overnight in saline at 37° C. Male Wistar rats aged 6 weeks were deeply anesthetized using intraperitoneal administration of a mixed anesthetic of midazolam (2 mg/kg), butorphanol (2.5 mg/kg), and medetomidine (0.15 mg/kg). The left sciatic nerve was exposed in a sciatic notch level, and 5 µL each of saline or 2% LPC (Sigma-Aldrich) was administered to a proximal sciatic nerve with the use of a Hamilton syringe. After 7 days from administration of LPC, either a saline-filled osmotic pump or a present extract-filled osmotic pump (24 NU/kg/day) was placed subcutaneously in the back of rats, and saline or the present extract was continuously administered for the following one week.

(2) Evaluation of Sciatic Function Index

To evaluate the motor function, a sciatic function index (SFI) was measured 2 weeks after the operation. For measurement of SFI, ink was applied to the soles of hind paws of rats, and office paper was placed on a level pedestal of 40 cm-square, and rats were allowed to walk on the office paper and the footprints were recorded. The following parameters were measured, and SFI was calculated according to the following formula. SFI=0 indicates normal, and SFI=−100 indicates complete loss of function. An individual in which necrosis or defect occurred in the paw during the postoperative course was excluded.

<SFI Numerical Formula>

$$SFI=-38.3\times((EPL-NPL)/NPL)+109.5\times((ETS-NTS)/NTS)+13.3\times((EITS-NITS)/NITS)-8.8$$

<Each Item>
EPL=experimental print length
NPL=normal print length
ETS=experimental toe spread
NTS=normal toe spread
EITS=experimental intermediary toe spread
NITS=normal intermediary toe spread Test Result One example of the result of the above test is shown in FIG. 3. Significant improvement in SFI was observed and the motor function improved in the demyelination present extract administration group compared with the demyelination control group.

(3) Von Frey Test

To evaluate the sensory function, at 2 weeks after the operation, hind paw withdrawal thresholds to mechanical stimuli (mechanical hind paw withdrawal thresholds) were measured both on the unaffected side and the affected side by using von Frey filaments (0.008 g to 26 g, North Coast Medical) in the same manner as in the above Test example 1(2), and the affected side/unaffected side ratio was calculated and evaluated.

Test Result

One example of the result of the above test is shown in FIG. 4. In the von Frey test, significant improvement was observed and the paresthesia (hypesthesia) ameliorated in the demyelination present extract administration group compared with the demyelination control group.

(4) Hot Plate Test

To evaluate the response to a thermal stimulus, at 2 weeks after the operation, the time until the animal shows the first avoiding reaction of the affected paw (licking or raising the affected paw) (Hot plate latency) was measured at a setting of 52.5° C. by using a hot plate device (Ugo Basile). The cutoff time was 45 seconds.

Test Result

One example of the result of the above test is shown in FIG. 5. In the hot plate test, significant improvement was observed and the thermal paresthesia (hypesthesia) ameliorated in the demyelination present extract administration group compared with the demyelination control group.

(5) Electrophysiological Evaluation

Rats after a lapse of 2 weeks from the operation were sedated with an anesthetic, and placed in the prone position on the operating table, and the left sciatic nerve and the left tibialis anterior were exposed. CMAP and TL were measured by stimulating the proximal side of the sciatic nerve with a bipolar electrode. Stimuli were applied on a proximal side and on a distal side of the sciatic nerve crush injury site with a bipolar electrode, and NCV was calculated from the respective measurements in the same manner as in the above Test example 1(3). For measurement and evaluation, PowerLab 2/26 (AD Instruments) was used in the same manner as in the above Test example 1(3).

Test Result

One example of the result of the above test is shown in FIGS. 6, 7, and 8. In all of NCV, CMAP, and TL, significant improvement was observed and the electrophysiological functions improved in the demyelination present extract administration group compared with the demyelination control group.

(6) Immunohistological Evaluation

Rats after a lapse of 2 weeks from the operation were sedated with an anesthetic, and sciatic nerves were sampled. Sciatic nerves were fixed in 4% paraformaldehyde for 24 hours at room temperature, then dipped in 20% sucrose liquid, embedded in a Tissue-Tec (Sakura Finetek Japan), and frozen in liquid nitrogen, and a frozen section of the cross section of 5 µm thick was prepared. The frozen section was permeabilized with 100% methanol for 30 minutes at −20° C., and blocked with PBS+0.2% TritonX+5% bovine serum albumin. Then the section was caused to react overnight at 4° C. with anti-NF200 rabbit antibody (1:1000; 102M4784, Sigma-Aldrich) and an anti-MBP mouse antibody (1:1000; NE1018, CALBIOCHEM) as primary antibodies. After the reaction, the section was caused to react with Alexa 488-labeled goat anti-rabbit IgG antibody (1:1000; Lifetechnologies) and Alexa 568-labeled goat anti-mouse IgG antibody (1:1000; Lifetechnologies) as secondary antibodies for 1 hour. After reaction with the secondary antibodies, the section was caused to react with a mounting medium (product name: Perma fluor [registered trademark], Thermo Fisher Scientific) containing DAPI (4'-6-diamidino-phenyl-2-indole, Wako Pure Chemical) for evaluation of nuclei. The ratio of myelinated axons (the number of MBP positive axons)/(the number of total axons) was evaluated by using NIS Elements BR software (Nikon).

Test Result

One example of the result of the above test is shown in FIG. 9. Significant increase was observed in the number of MBP positive axons relative to the number of total axons, and the demyelination symptom ameliorated in the demyelination present extract administration group compared with the demyelination control group.

Statistical Analysis

In Test example 1 and Test example 2, statistical analysis was performed by Tukey-Kramer HSD test using JMP software version 11 (SAS Institute). $p<0.05$ was regarded as "significant".

Test Example 3 Evaluation in Paclitaxel-Induced Rat Peripheral Nerve Disorder Model The effect of the present extract on the peripheral nerve disorder which is a side effect associated with administration of paclitaxel was investigated. Paclitaxel is an anticancer agent. The present extract was continuously administered to rats by using an osmotic pump, and a Von Frey test was conducted.

(1) Preparation of Paclitaxel-Induced Peripheral Nerve Disorder Rats and Administration of Present Extract In the same manner as in Test example 1, an osmotic pump (product name: alzet [registered trademark], model: 2ML2, product of DURECT) was filled with saline or the present extract, and stood still overnight in saline at 37° C. Paclitaxel (2 mg/kg) was intraperitoneally administered to male SD rats aged 6 weeks every other day a total of four times to prepare paclitaxel-induced peripheral nerve disorder rats. For the normal control group, a mixed solution of polyoxyethylene castor oil which is a solvent of paclitaxel, and ethanol in a volume ratio of 1:1 was further diluted three-fold with saline, and administered in the same manner as paclitaxel. After 2 weeks from the start of administration of paclitaxel, a saline-filled osmotic pump for the normal control group and the onset control group, or an osmotic pump filled with the present extract (8.0 NU/kg/day) for the present extract osmotic pump administration group was placed subcutaneously in the back of rats. The saline or the present extract was continuously administered by indwelling the osmotic pumps for 2 weeks.

(2) Repetitive Oral Administration of Present Extract

The repetitive oral administration group of the present extract underwent repetitive oral administration of the present extract (200 NU/kg/day) for 2 weeks from 14 days after the start of administration of paclitaxel.

(3) Von Frey Test

Rats of the above (1) were put into a transparent acryl cage with a metal gauze bottom, and conditioned for about 3 minutes, and then 50% withdrawal thresholds to mechanical stimuli of right hind paws were measured by using the von Frey filaments (0.4-15.0 g, North Coast Medical), and mean±standard error of each group was calculated. After 25 days from the start of administration of paclitaxel (after 11 days from the start of administration of the present extract), 50% withdrawal thresholds to mechanical stimuli of right hind paws were measured at the start of oral administration of the present extract (200 NU/kg/day) and 1, 4 and 24 hours after administration. Subsequently, for the remaining three groups (normal control group, onset control group, and present extract-filled osmotic pump administration group), 50% withdrawal thresholds to mechanical stimuli were measured.

Statistical Analysis

In Test example 3, statistical analysis was performed by F test for comparison between two groups using SAS System Version 9.1.3 (SAS Institute), or by Student's t-test in the case of equal variance, or by Welch test in the case of unequal variance. $p<0.05$ was regarded as "significant".

Test Result

One example of the result of the above test is shown in FIG. 10. After 25 days from the start of administration of paclitaxel (time point 0 on the horizontal axis in FIG. 10), the 50% withdrawal threshold to mechanical stimuli in the present extract-filled osmotic pump administration group significantly increased compared with the onset control group. Also, the 50% withdrawal threshold to mechanical stimuli in the present extract repetitive oral administration group significantly increased after 25 days from the start of administration of paclitaxel, compared with the onset control group. While the dose of the present extract was 8.0 NU/kg/day in the present extract-filled osmotic pump administration group, and 200 NU/kg/day in the present extract repetitive oral administration group, the effects in these groups were nearly equivalent. Although there is a difference between the subcutaneous administration and the oral administration, the continuous administration of the present extract by means of the osmotic pump showed very high effect.

Examples of the method for administering the present preparation to a patient (human) in need of a treatment include intravenous, subcutaneous, and intramuscular administrations of injections, and oral administration of tablets. While the dose can be appropriately set, a dose accepted for the commercially available present preparation (NEUROTROPIN [registered trademark]) is normally 3.6 to 7.2 NU per day for injections, and 16 NU per day for oral preparations (tablets). These doses converted to doses for a human weighing 60 kg are 0.06 to 0.12 NU/kg/day for injections, and about 0.27 NU/kg/day for oral preparations (tablets). "NU" is an abbreviation for "NEUROTROPIN unit", and "NEUROTROPIN unit" is defined by an $ED_{50}$ value of the analgesic effect, determined by a test in accordance with a modified Randall-Selitto method using a SART stress mouse, which is a chronic stress animal having a lowered pain threshold than normal animals. "1 NU" is an activity indicating 1 mg of an analgesic activity containing component of a NEUROTROPIN preparation when the $ED_{50}$ value is 100 mg/kg. In "Nabutopin" [registered trademark] which is a generic drug of NEUROTROPIN injections, or "Analgecine" [registered trademark] which is an analogous drug of NEUROTROPIN, "unit" is used, and the "unit" is substantially the same meaning as "NEUROTROPIN unit". Therefore, in the present application, "unit" is employed.

According to the results of the experiments of subcutaneously administering the present extract to rats of Example 2 (Test examples 1 to 3) by using a continuous administration device, effective doses of the present extract were 12 NU/kg/day (Test example 1), 24 NU/kg/day (Test example 2) and 8.0 NU/kg/day (Test example 3). Therefore, as the range of the effective amount of the present extract when the continuous administration device is used, 8.0 to 24 NU/kg/day can be one standard. However, since this is a standard for rat, it is naturally considered that the range differs depending on the animal species. While the effective dose in the oral administration in rat performed in Test example 3 is 200 NU/kg/day, from the experience of the applicant who has performed the test of administering the present extract or the like to animals for a long time, it is often the case that the effect is observed when the dose is 100 to 200 NU/kg/day in the case of orally administering the present extract or the like. In simple comparison, in subcutaneous administration using a continuous administration device in rat, one fourth (24÷100) to one twenty-fourth (8.0÷200) as the dose of the present extract in oral administration suffices. On the other hand, a dose accepted for the commercially available present preparation (NEUROTROPIN [registered trademark]) is about 0.27 NU/kg/day for oral preparations (tablets) as described above. Thus, in the case of oral administration, the effective dose is estimated to be higher in rat than in human by about 370 (100÷0.27) to 740 (200÷0.27) times (in human, effective with a dose of one 370 to 740th in rat). Therefore, as a dose in the case of administering the present extract or the like to a human by using a continuous administration device, a value of about 0.011 to 0.065 NU/kg/day is calculated by dividing 8.0 to 24 NU/kg/day obtained for rat by 370 to 740.

On the other hand, from the experience of the applicant, it is often the case that the effect is observed with an amount of 5 to 100 NU/kg/day when the present extract or the like is (intravenously, subcutaneously, intraperitoneally) injected to animals. A dose accepted for injections of the commercially available present preparation (NEUROTROPIN [registered trademark]) is 0.06 to 0.12 NU/kg/day as described above. Thus, in the case of administration by injection, the effective dose is estimated to be higher in rat than in human by about 42 (5÷0.12) to 1670 (100÷0.06) times (in human, effective at a dose of one 42 to 1670th in rat). Therefore, as a dose in the case of administering the present extract or the like to a human by using a continuous administration device, a value of about 0.005 to 0.57 NU/kg/day is calculated by dividing 8.0 to 24 NU/kg/day obtained for rat by 42 to 1670.

From the foregoing, preferred embodiments of the present invention include the following. However, it is to be noted that the present invention is not limited to these embodiments.

(1) A test method for an action of an extract from inflamed skin tissues inoculated with vaccinia virus or a preparation containing the extract, by sustainedly administering the extract or the preparation containing the extract to an animal (other than human) by a continuous administration device.
(2) The test method according to (1), wherein the continuous administration device is of a type that is attached outside the body of the animal, or of a type that is embedded inside the body of the animal.
(3) The test method according to (1), wherein the continuous administration device is of a type that is embedded inside the body of the animal.
(4) The test method according to (2) or (3), wherein the continuous administration device that is embedded inside the body of the animal is an osmotic pump.
(5) The test method according to any one of (1) to (4), wherein a dose of the extract from inflamed skin tissues inoculated with vaccinia virus or the preparation containing the extract is 0.2 to 1000 units/kg/day.
(6) The test method according to any one of (1) to (4), wherein a dose of the extract from inflamed skin tissues inoculated with vaccinia virus or the preparation containing the extract is 5 to 30 units/kg/day.
(7) The test method according to any one of (1) to (4), wherein a dose of the extract from inflamed skin tissues inoculated with vaccinia virus or the preparation containing the extract is 10 µL to 50 mL/kg/day.
(8) The test method according to any one of (1) to (4), wherein a dose of the extract from inflamed skin tissues inoculated with vaccinia virus or the preparation containing the extract is 100 to 300 µL/kg/day.
(9) The test method according to any one of (1) to (8), wherein a dosing period of the extract from inflamed skin tissues inoculated with vaccinia virus or the preparation containing the extract is 1 day to 6 months.
(10) The test method according to any one of (1) to (8), wherein a dosing period of the extract from inflamed skin tissues inoculated with vaccinia virus or the preparation containing the extract is 3 days to 2 months.
(11) The test method according to any one of (1) to (10), wherein the action is an action on sensory function, an action on motor function, an action on electrophysiological function, or an action on demyelination symptom in a peripheral nerve.
(12) The test method according to any one of (1) to (11), wherein the inflamed skin tissues are inflamed skin tissues of a rabbit.
(13) Use of an extract from inflamed skin tissues inoculated with vaccinia virus or a preparation containing the extract by a continuous administration device.
(14) Use according to (13), wherein the inflamed skin tissues are inflamed skin tissues of a rabbit.
(15) An extract from inflamed skin tissues inoculated with vaccinia virus or a preparation containing the extract, that is continuously administered.
(16) The preparation according to (15), that is an analgesic.
(17) The preparation according to (16), that is a therapeutic or alleviating agent against acute or chronic pain due to peripheral nerve disorder.
(18) The preparation according to (15), that is a therapeutic or alleviating agent for peripheral nerve disorder.
(19) The preparation according to (18), wherein the peripheral nerve disorder is caused by an anticancer agent.
(20) The preparation according to (19), wherein the peripheral nerve disorder caused by an anticancer agent is acute or chronic pain, numbness, paresthesia, hyperesthesia, or sensory abnormality.
(21) The preparation according to any one of (15) to (20), wherein the inflamed skin tissues are inflamed skin tissues of a rabbit.
(22) The preparation according to any one of (15) to (21), wherein continuous administration is performed by a continuous administration device.
(23) The preparation according to any one of (15) to (22), wherein a dose is 0.001 to 1 unit/kg/day.
(24) The preparation according to any one of (15) to (22), wherein a dose is 0.005 to 0.6 units/kg/day.
(25) The preparation according to any one of (15) to (24), wherein a dosing period is 1 day to 6 months.
(26) The preparation according to any one of (15) to (24), wherein a dosing period is 3 days to 2 months.

(27) A therapeutic or alleviating method for pain, wherein an extract from inflamed skin tissues inoculated with vaccinia virus or a preparation containing the extract is continuously administered.

(28) The therapeutic or alleviating method according to (27), wherein the pain is acute or chronic pain due to peripheral nerve disorder.

(29) A therapeutic or alleviating method for peripheral nerve disorder, wherein an extract from inflamed skin tissues inoculated with vaccinia virus or a preparation containing the extract is continuously administered.

(30) The therapeutic or alleviating method according to (29), wherein the peripheral nerve disorder is caused by an anticancer agent.

(31) The therapeutic or alleviating method according to (30), wherein the peripheral nerve disorder caused by an anticancer agent is acute or chronic pain, numbness, paresthesia, hyperesthesia, or sensory abnormality.

(32) The therapeutic or alleviating method according to any one of (27) to (31), wherein the inflamed skin tissues are inflamed skin tissues of a rabbit.

(33) The therapeutic or alleviating method according to any one of (27) to (32), wherein continuous administration is performed by a continuous administration device.

(34) The therapeutic or alleviating method according to any one of (27) to (33), wherein a dose is 0.001 to 1 unit/kg/day.

(35) The therapeutic or alleviating method according to any one of (27) to (33), wherein a dose is 0.005 to 0.6 units/kg/day.

(36) The therapeutic or alleviating method according to any one of (27) to (35), wherein a dosing period is 1 day to 6 months.

(37) The therapeutic or alleviating method according to any one of (2) to (35), wherein a dosing period is 3 days to 2 months.

INDUSTRIAL APPLICABILITY

As described above, it was revealed that continuous administration using an osmotic pump exerts excellent action at a low dose compared with the conventional administration methods. From this result, it has been considered that administration of the present extract can reduce the dose and the frequency of administration, and can be an effective test method capable of reducing the amount of work of a researcher. It has been also considered that the sustained administration preparation of the present extract can reduce the dose and the frequency of administration, and can be a preparation effective for improvement in medication compliance of a patient.

The invention claimed is:

1. A test method for an action of an extract from inflamed skin tissues inoculated with vaccinia virus or a preparation containing the extract, the method comprising:
sustainedly administering the extract or the preparation containing the extract to a non-human animal using a continuous administration device,
wherein the animal is in need of treatment comprising an action on sensory function, an action on motor function, an action on electrophysiological function, or an action on demyelination symptom in a peripheral nerve.

2. The test method according to claim 1, wherein the continuous administration device is of a type that is attached outside the body of the animal, or of a type that is embedded inside the body of the animal.

3. The test method according to claim 2, wherein the continuous administration device that is embedded inside the body of the animal is an osmotic pump.

4. The test method according to claim 1, wherein the continuous administration device is of a type that is embedded inside the body of the animal.

5. The test method according to claim 1, wherein a dose of the extract from inflamed skin tissues inoculated with vaccinia virus or the preparation containing the extract is 0.2 to 1000 units/kg/day.

6. The test method according to claim 1, wherein the inflamed skin tissues are inflamed skin tissues of a rabbit.

* * * * *